United States Patent [19]

Abo El-Nil

[11] 4,353,184
[45] Oct. 12, 1982

[54] METHOD FOR ASEXUAL REPRODUCTION OF CONIFEROUS TREES

[75] Inventor: Mostafa M. Abo El-Nil, Milton, Wash.

[73] Assignee: Weyerhaeuser Company, Tacoma, Wash.

[21] Appl. No.: 263,969

[22] Filed: May 18, 1981

[51] Int. Cl.$^3$ .............................................. A01G 1/00
[52] U.S. Cl. ....................................................... 47/58
[58] Field of Search ............................................ 47/58

[56] References Cited

U.S. PATENT DOCUMENTS 4,217,730  8/1980  El-Nil ...................................... 47/58

OTHER PUBLICATIONS

"First Morphological Evidence . . . ," Franclet et al, Comptes Rendus 290, Series D:927–930, 1980.
"In Vitro Phyllomorphic . . . ," Jansson et al, Physiol. Plant., 49:105–111, 1980.
"Potential for Forest . . . ," Karnosky, Bioscience 31(2):114–120, 1981.
"Vegetative Propagation . . . ," Marino et al, Proc. of the Plant Growth Regulator Working Gp., 4th Ann. Mtg., Aug. 9–11, 1977, p. 286.
"Shoot Apex Development . . . ," Cohen, J. Amer. Soc. Hort. Sci., 103:483–484, 1977.
"Effect of N$^6$-BA, GA$_3$ . . . ", Cohen et al, J. Amer. Soc. Hort. Sci., 100:404–406, 1975.
"Obtention de Plants . . . ," David et al, Comptes Rendus 287, Series D:245–248, 1978.
"Rajeunissment des arbres . . . ," Franclet, Micropropagation d'arbres Forestiers, AFOCEL: Etudes et recherches, No. 12: 3–18, 1979.
"Hormonal Control . . . ", Mehra–Paltra et al, 1977, TAPPI for Biol. Wood Chem. Conf., Madison, Wisconsin, pp. 15–20.
"Callus & Adventitious . . . ," Minocha, 1980, Can. Journ. Bot., 58:366–370.
"Application of Tissue . . . ," Sommer et al, 1979, Plant Cell & Tissue Culture, Ohio State Univ. Press, pp. 461–491.
"Vegetative Propagation . . . ," Whitehill et al, 1975, Physiol. Plant. 35:66–71.

Primary Examiner—Robert E. Bagwill

[57] ABSTRACT

This invention is a method for asexual reproduction of coniferous trees. It combines in vivo hormone treatments with in vitro tissue culture for multiplication of a clone of the original genotype. The first step is repetitive cytokinin treatment of the living tree, preferably on weekly intervals. This will induce buds or shoots, usually in axillary locations or at the apex of fascicles. These shoots have a morphology typical of juvenile plants or even newly sprouted seedlings. In culture, the buds will give rise to juvenile-like shoots. The shoots or buds are placed in various media to induce growth and further budding. These second order buds are again placed in a growth medium to give rise to shoots that can then be rooted. The method appears unique in its ability to rapidly and inexpensively multiply a large clone of genotypically superior trees of physiologically and morphologically mature age.

20 Claims, 1 Drawing Figure

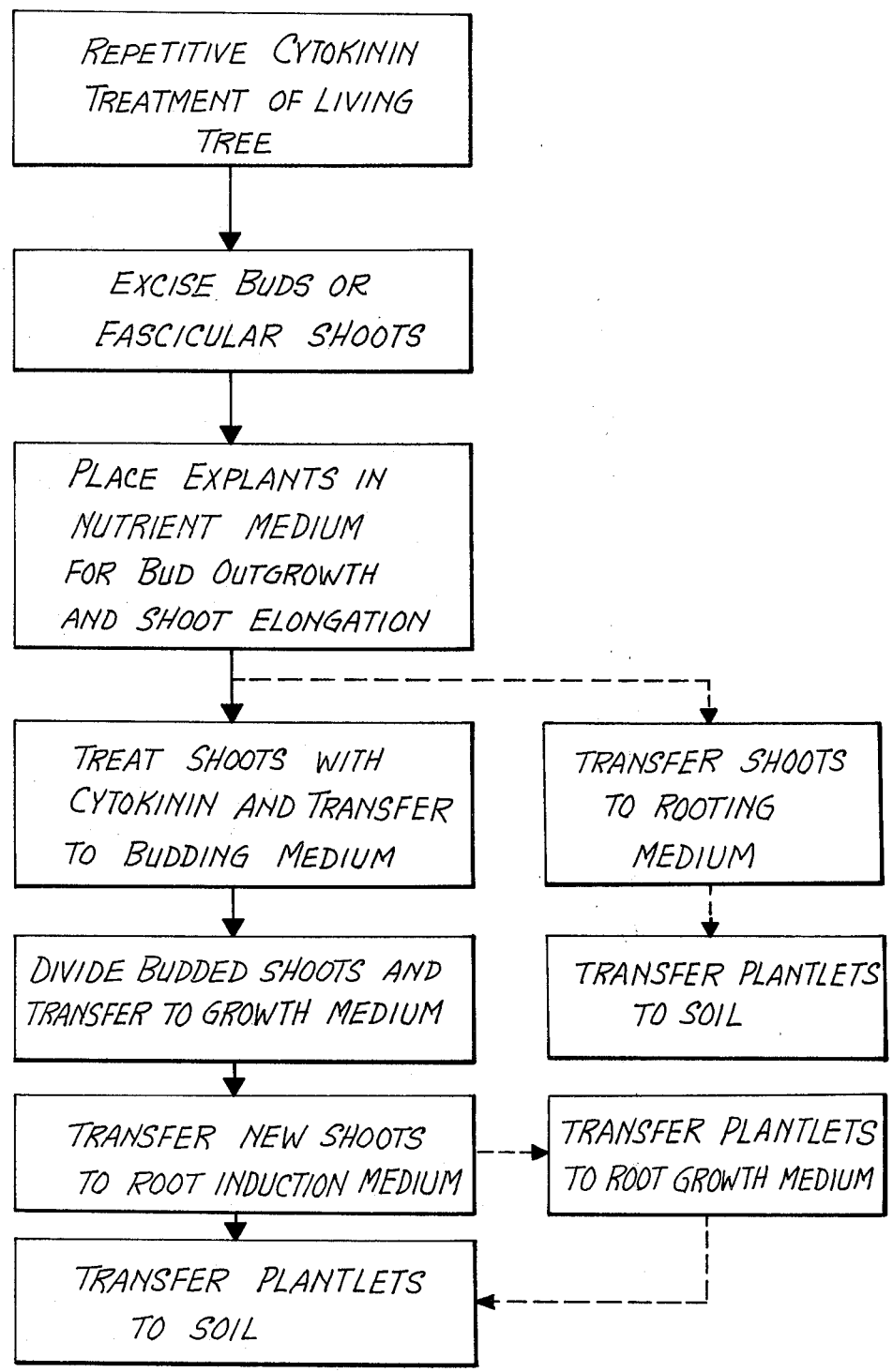

METHOD FOR ASEXUAL REPRODUCTION OF CONIFEROUS TREES

FIELD OF THE INVENTION

This invention relates to the asexual reproduction of coniferous trees. It is particularly applicable to the reproduction of genotypically superior trees of important forest species. The method appears applicable to older tissue as well as to that of very young trees.

BACKGROUND OF THE INVENTION

For many years the forest products industry did not concern itself with its future wood supply, since the American forests were seen as being inexhaustable. It was not until well into the second quarter of this century that it became painfully apparent to a few farsighted forest managers that this was not the case. The first commercial tree farm established in 1941 marked a major turning point in attitudes.

Initially cut over land was restocked by leaving individual trees or blocks of trees as a seed source. In many cases the land would become overgrown with brush or undesirable tree species since good seed crops on most coniferous species occur only at infrequent intervals. Later, natural seeding was supplemented by aerial seeding and by hand planting seedlings grown in large nurseries.

Originally, nurseries had to draw exclusively on wild seed supplied by individual collectors. Only in the last 20 years has serious consideration been given to genetic improvement of the forest crop. To date this has largely been implemented by creation of seed orchards based on grafted scions from naturally occurring superior trees. A few second generation orchards are now in production based on trees produced by selective crossing of improved genotypes.

Unfortunately, achieving genetic gain in trees is a slow process because of the long crop cycles necessitated by slow sexual maturation. It has long been apparent that the gain could be accomplished much more rapidly if trees for restocking could be reproduced asexually. Grafting has proved far too slow and expensive for forest restocking, since many hundreds of millions of tree seedlings are planted each year. Reproduction through tissue culture has been an attractive possibility. However, the coniferous trees have been so difficult to reproduce in culture that even with breakthrough discoveries for some species made about 1975, the process still is not commercial. One major roadblock has been the difficulty in culturing anything but very young tissue. A preferred explant has been cotyledon or hypocotyl tissue from newly sprouted seeds. Workers have had minor success on some species, or on some genotypes within species, with trees up to 2-3 years of age. But the success has not been achieved with sufficient consistency for commercial application. Only with coast redwood, *Sequoia sempervirens*, can culture of trees from older trees be considered as successful [Jansson and Bornman, *Physiol. Plant.* 49:105-111 (1980)].

There are many advantages inherent in culturing tissue from older trees. A principal one is that it may take from five to 20 years before the phenotypic expression of an individual genotype can be adequately judged. This is as yet virtually an impossibility for younger trees. A number of investigators have recently summarized the state of the art in culturing older tissue and all point to the difficulty of the problems yet to be solved [Sommer and Brown in *Plant Cell and Tissue Culture: Principles and Applications*, Sharp et al., eds., pp. 461-491, Ohio State University Press (1979); Minocha, *Can. J. Bot.* 58:366-370 (1980); Karnosky, *Bio Science* 31(2):114-120 (1981)].

Despite the difficulties, some progress has been made in asexual reproduction of older wood. The work has been largely directed to various species of Pinus and two approaches might be noted. One done in vivo involves treating living trees with hormones to induce shoots from latent fascicular buds. A cytokinin is always present and other hormones may be used as well. Any shoots that form are excised and placed in a rooting mixture. This approach is exemplified in work reported by Whitehill and Schwabe, *Physiol. Plant.* 35:66-71 (1975); Cohen and Shanks, *J. Amer. Soc. Hort. Sci.* 100:404-406 (1975); Marino, Shahan, and Greenwood, *Proc., Plant Growth Regulator Working Group*, Fourth Annual Meeting (1977); and Cohen, *J. Amer. Soc. Hort. Sci.* 103:483-484 (1978). The success of this approach has been inconsistent but, in general, the percentage of shoots ultimately rooted has been low.

The second approach done in vitro involves excision of fascicles and placing them, at least initially, in a culture medium containing a cytokinin. This treatment also induces formation of the latent bud at the apex of the fascicle. The budded fascicles can then be placed in another medium to induce shoot growth. Finally the shoots are placed in a rooting medium or mixture. Recent examples of this approach are Mehra-Palta, Smeltzer, and Mott, TAPPI Forest Biology Wood Chemistry Conference, Madison, Wisc (1977): David, Isemukali and David, *Comptes Rendus*, Series D, 287:245-248 (1978); Franclet, David, David, and Boulay, *Comptes Rendus*, Series D, 290:927-930 (1980); and Franclet in *Micropropagation d'arbres forestiers, AFOCEL: Etudes et Recherches*, No. 12:3-18 (1979).

Because of the more rapid growth of young trees grown from seeds, an additional goal of asexual reproduction from mature trees has been rejuvenation. The first steps toward this goal are apparent in the work of the French investigators cited above. Yet even with the initial progress of the last few years, a wholly practical system for asexual reproduction from coniferous trees of the very large quantities of plants or plantlings suitable for mass forest regeneration has yet to be found, prior to the present invention.

SUMMARY OF THE INVENTION

The present invention relates to the asexual reproduction of coniferous trees. It comprises a combination of which the first step is repetitive cytokinin hormone treatments of the living tree. This induces the formation of buds or shoots, at least some of which will have a juvenile-like morphology. The shoots, or short sections of the stems containing the buds, are then placed on a nutrient culture medium to induce growth. Here, the buds burst and elongate into shoots, or the shoots further elongate. The new growth has and retains a morphology that is juvenile in appearance. While the new shoots may at this point be put into a rooting mixture or medium, it is preferred that they be further multiplied in vitro. To accomplish this, they are removed from the growth medium and placed in another medium whose nutritional makeup encourages budding. A one-time cytokinin treatment given to the tissue between these two media is often advantageous. Buds will form in the needle axils or, in some cases, adventitious buds will form on the shoots or needles themselves. When the buds have reached an adequate size, the shoots are divided into smaller sections and again placed on a growth medium that promotes bud burst and shoot elongation. At this point, the shoots are normally excised and placed in a medium containing auxins to induce rooting. Ultimately they are removed from medium and planted in soil or a growing mixture until they have attained sufficient size for transplanting into the field.

The particular procedure to be used will depend somewhat on the characteristics of the individual species being reproduced. Species within the families Pinaceae, Cupressaceae, Taxodiaceae, or Araucariaceae appear to respond well to the treatment described. In particular, trees within the genera Pinus, Picea, Tsuga, Pseudotsuga, Thuja, Juniperus, Sequoia, and Araucaria have shown excellent response and apparent rejuvenation. Pinus will behave somewhat differently from most other members of the Pinaceae because its needles are borne on fascicles which contain a latent bud meristem at the base of the needle cluster. It is this bud that is normally activated by the in vitro cytokinin treatment. In the other genera within the Pinaceae it is usually a latent axillary bud meristem that is activated. Typically, the pines will form actual fascicular shoots in response to the initial cytokinin treatment, while the other Pinaceae genera will form axillary buds. The response will be somewhat different with Sequoia or with Thuja where epicormic and other adventitious budding occurs at less well-defined sites.

It is thus an object of the present invention to produce plantlings from coniferous trees by a combination of in vivo hormone treatment of the trees and in vitro culture of the hormone-induced growth.

It is a further object to produce plantlings having juvenile-like characteristics from morphologically mature coniferous trees.

It is still a further object to produce plantlings from coniferous trees that have attained an age at which asexual reproduction has a low degree of success when conventional methods are used.

It is yet another object to provide a method whereby superior coniferous tree genotypes can be multiplied in the large quantities necessary to aid in reforestation of land whose productive potential is not being fully used.

These and other objects will become readily apparent on reading the following detailed description of the invention in conjunction with the accompanying drawing.

BRIEF DESCRIPTION OF THE DRAWING

The single FIGURE is a block diagram showing preferred and alternate process steps by which the present invention can be carried out.

DETAILED DESCRIPTION OF THE PREFERRED EMBODIMENTS

A number of the botanical terms used in this patent specification are occasionally found to have different meanings in the literature. The following definitions of certain terms used in this patent specification are the ones most commonly used in the field of botany.

"Tissue culture" is the process by which tissue excised from a donor plant is nourished on a series of culture media to produce plantlets genetically identical to the donor.

A "plantlet" is a plant asexually reproduced by tissue culture.

A "plantling" is a plantlet growing in a soil mixture that has attained sufficient size and hardiness to be outplanted.

A "meristem" is a group of tissue-forming cells capable of further directed development into plant organs; e.g., shoots and roots.

"Adventitious" refers to organs that develop in abnormal and unpredictable locations, where organ primodia do not normally exist.

An "epicormic" bud is an adventitious bud occurring on the main or secondary stems of a plant.

"Morphogenesis" refers to the origin and development of organs or parts of organisms.

"Organogenesis" is the formation and development of organs, such as buds, from meristemic centers in tissues that would not ordinarily organize into the particular organ.

An "explant" is a piece of tissue taken from a donor plant for culturing.

"Cytokinins" are plant hormones that effect the organization of dividing cells and function in the transmission of information from DNA for protein formation.

"Auxins" are plant hormones that promote cell division and growth.

A "fascicle" is a very short, needle-bearing shoot or stem that will not normally show growth beyond its first season. The terms spur shoots, short shoots, dwarf shoots, needle bundles, and brachyblasts are synonymous with fascicle.

"Axillary" is the location on the up-stem side of a leaf or needle at junction with its supporting stem. An "axiallary bud" is an actual or latent meristemic bud in an axillary location.

A seedling or very young plant will exhibit "juvenile morphology" in formation and appearance. A "primary stem" as herein used is one exhibiting juvenile or juvenile-like morphology.

Plants beyond their first or second year of age generally exhibit "adult morphology" in their appearance. In a pine, for example, a plant having adult morphology will have clusters of needles borne on fascicles while one showing juvenile morphology will typically have single needles attached directly to the stem.

In its preferred form, the invention involves treating the tissue donor tree while in the dormant state, but with an artificially increased temperature and photoperiod, with weekly spray or dip treatments of a cytokinin solution. Most conveniently the donor trees will be potted and of a size which can be brought into a greenhouse. For many large trees it is often possible to graft a scion to a smaller root stock to create a donor which is more easily treated.

$N^6$-Benzyladenine (or benzylaminopurine), hereafter BA, is a preferred cytokinin. However, other cytokinins such as kinetin (6-furfurylaminopurine), or 2-IP ($N^6$-isopentenylaminopurine) may be used. The choice will depend somewhat on the response of the particular species being treated and this can be readily determined experimentally. Other growth regulators may also be used in combination with the cytokinin. For example, with Douglas-fir (*Pseudotsuga menziesii*) and some other species, an enhanced response is noted when a minor percentage of N-dimethylaminosuccinamic acid is used with BA.

The whole tree may be treated, or only individual branches. This may be done by dipping, spraying, or direct infusion into the vascular system of the tree as, for example, through the end of a cutoff stem. If dipping or spraying is chosen, a sufficient amount of the cytokinin solution is applied to cause runoff. The time between treatments is not highly critical and one week intervals are not only a period of convenience, but appear to give excellent results. The treatment period probably should not be shorter than every four to five days, since the hormone treatments can then cause phytotoxicity. The necessary cumulative effect of the cytokinin treatment is not fully realized if the treatments are made at much more than 14-day intervals.

The number of in vivo cytokinin treatments necessary will depend on a number of factors. The particular species or even the individual genotype, the state of dormancy, the cytokinin being used, and the interval between treatments all will have some effect. Usually, treatments at weekly intervals will produce the results desired. This can be readily determined visually.

In the following examples, all of the trees were sprayed with the following solution at weekly intervals: BA 200 mg/L, dimethylsulfoxide 0.5 g/L, Tween 20 2 drops/L. Tween is a trademark of ICI Americas, Inc., Wilmington, Delaware, for a polyoxyethylene sorbitan monolaurate nonionic surfactant.

BA has been found to be effective in the range of about 50 mg/L to 1000 mg/L, although a concentration of about 200 mg/L is preferred. This corresponds roughly to a range of $0.5 \times 10^{-3}$ moles/L to $0.5/10^{-2}$ moles/L. It is preferred that the concentration of cytokinin should not be below $10^{-4}$ moles/L.

For trees within the genus Pinus, a noticeable swelling of the bases of the fascicles will typically occur after about 4 cytokinin spray treatments. After about the sixth treatment, from 1 to 10 small primary or juvenile-type shoots will emerge from the needle clusters on the fascicles. These shoots will have very small axillary buds, or clusters of axillary buds, at the needle bases. For Pinus it is desirable to allow about eight weeks after the last spray treatment before the shoots are cut as explants for further culture in vitro.

Where the cytokinin treatment is carried out on trees lacking fascicles, such as Picea or Pseudotsuga, the response will be the formation of axillary buds or bud clusters. For these trees no extended time period is required after organogenesis is noted and the shoot bearing the buds can be put directly into culture. The same procedure holds true for those families having scale-like needles, for example, trees from the genera Thuja or Araucaria. The morphogenetic response of these is frequently one of epicormic or other unpredictable bud formation followed by rapid bud break and sprouting. In this case, either the tissue bearing the buds or the juvenile-like sprouts themselves can be put into culture.

Reference to the figure will outline the route to be followed once the tissue is placed in vitro. The tissue is first sterilized and placed on a nutrient culture medium. This will generally lack exogeneous phytohormones, but some species may perform better if small amounts of hormones are present. Here, the shoots are allowed to elongate until they reach about 4 cm in length. In the case where budded tissue is placed in the growth medium, the buds will swell and burst and elongate into primary or juvenile-type shoots 3-4 cm long.

Two routes can now be followed. If only a small number of plants are needed, the elongated shoots can be placed directly in an auxin-containing root induction medium. The resulting plantlets can then be removed from the medium and planted in a natural or synthetic soil for further growth into plantlings. Preferably, they are transferred to an additional medium that will cause more vigorous root growth.

In most cases, it is preferred to achieve additional mutliplication of the clone. When this is desired, the new shoots are removed from the growth medium and placed on a bud induction medium. An intermediate cytokinin treatment is normally necessary. It is preferred to merely dip the shoot in a sterile solution of BA at a concentration of about 50 mg/L. Alternatively, the shoots can be placed on a cytokinin-containing medium for bud induction. Best results have usually been attained using the dip treatment and a hormone-free induction medium, however.

After an adequate period of time in the bud induction medium, buds will form predominantly as clusters at needle axils. As many as 160 buds have been observed on a single 4 cm long juvenile-like shoot of Pinus taeda. The budded shoots are then cut into sections at the internodes and transferred once more to a shoot elongation medium which usually will lack exogenous hormones. The buds will again swell, burst, and form juvenile-like shoots. When these have sufficiently elongated they are placed on an agar root induction medium containing an auxin or the multiplication cycle can again be repeated. Treatment from this point on is as was described earlier for the production of plantlets.

The following examples, using species from several families of coniferous trees, will serve to describe the best mode known to the inventor of practicing the invention.

EXAMPLE 1

The tissue donor trees were winter dormant loblolly pines (Pinus taeda) that had been rooted as cuttings from 5-year-old trees and had a physiological age of about 6-½ years. These were placed in a greenhouse under a 20-hour photoperiod at temperatures varying between about 24° C. and 29° C. The trees were sprayed weekly to runoff with the 200 mg/L BA solution described earlier. After the fourth spray there was a noticeable swelling of the fascicles. After the sixth spray, shoots were emerging from the fascicles at the base of the needle clusters. These were allowed to elongate on the tree for an additional eight weeks without further hormone treatment. Each tree was fertilized bi-weekly with 200 mL of a fertilizer solution having a concentration of 2.3 g/L of 20/20/20 NPK.

The shoots were about 1.5 to 3 cm long at the time they were excised from the tree. Tiny axillary buds were present and it was apparent that the shoots were primary stems with a juvenile morphology. The shoots were washed in a 3% Alconox solution for three minutes (Alconox is a granular laboratory glassware cleaner and is a trademark of Alconox, Inc., New York, NY). The explants were then rinsed in running water for one hour. They were then sterilized in a solution of one part sodium hypochlorite household bleach in nine parts of water v/v for ten minutes. The sterilant and explants were placed in a small ultrasonic cleaning device for one minute of this time.

The media were prepared by adding appropriate quantities of salts, vitamins, and other nutrients, most of which were made up as the stock solutions described in Table I. The compositions of the various individual media used are given in Tables II and III in which Table II lists the mineral salt constituents and Table III the organic constituents. All media were autoclave sterilized for eight minutes at 121° C.

TABLE I

Stock Solution Makeup

| Solution Designation | Stock Compounds | g/L | Solution Designation | Stock Compounds | g/L |
|---|---|---|---|---|---|
| A | $NH_4H_2PO_4$ | 60.0 | I | $Na_2EDTA$ | 7.45 |
|   |   |   |   | $FeSO_4.7H_2O$ | 5.56 |
| B | $NH_4NO_3$ | 33.0 | J | $H_3BO_3$ | 1.0 |
| C | $KNO_3$ | 125.0 |   | KI | 0.2 |
|   |   |   |   | $NaMoO_4.2H_2O$ | 0.02 |
| D | $Ca(NO_3)_2.4H_2O$ | 120.0 |   | $CoCl_2.6H_2O$ | 0.02 |
| E | $CaCl_2.2H_2O$ | 40.0 | K | Myo-inosotol | 50 |
| F | $NaH_2PO_4.H_2O$ | 55.2 | L | Thiamine.HCl | 1.0 |
|   |   |   |   | Nicotinic Acid | 1.0 |
| G | $KH_2PO_4$ | 34.0 |   | Pyridoxine.HCl | 0.1 |
| H | $MgSO_4.7H_2O$ | 80.0 |   |   |   |
|   | $MnSO_4.H_2O$ | 2.0 |   |   |   |
|   | $ZnSO_4.7H_2O$ | 0.2 |   |   |   |
|   | $CuSO_4.5H_2O$ | 0.04 |   |   |   | photoperiod under cool white fluorescent lamps and an illumination level of 1076 lm/m².

When the explants had been in culture for six weeks they had elongated to about 4 cm in length. Facicles on the stems were rare and the leaves were predominantly single needles typical of the first true foliage on a seedling. At this time the shoots could be removed from the elongation medium and placed in the root induction medium of Tables II and III. If this route was chosen they would preferably then be placed in a root growth medium after roots appeared in order to insure greater vigor and a higher chance of survival when transferred into a growing medium of natural or synthetic soil.

In most cases it will be preferred to achieve greater multiplication since the use of the above alternate route yields only 1 to 10 ultimate plantlings per parent tree fascicle. To accomplish this, the elongated shoots are removed from the first elongation medium and preferably given a quick dip in a solution of 50 mg/L BA containing two or three drops/L of Tween 20. They are then placed base down in 25×115 mm sealed test tubes containing Bud Induction Medium-I to enable develop-

TABLE II

Salt Concentrations in *Pinus taeda* Culture Media[1]

| Compound | Shoot Elongation Medium-I | Bud Induction Medium-I | Bud Induction Medium-II | Shoot Elongation Medium-II | Root Induction Medium | Root Growth Medium |
|---|---|---|---|---|---|---|
| $NH_4H_2PO_4$ | — | 150 | — | 150 | — | — |
| $NH_4NO_3$ | — | — | 165 | — | — | 550 |
| $KNO_3$ | 1250 | 1250 | 1437.5 | 2500 | 187.5 | 633.3 |
| $Ca(NO_3)_2.4H_2O$ | — | — | 600 | — | 152 | 146.6 |
| $CaCl_2.2H_2O$ | 200 | 100 | — | 200 | — | — |
| $NaH_2PO_4.H_2O$ | 276 | — | — | 138 | 138 | — |
| $KH_2PO_4$ | — | — | 170 | — | — | 56.6 |
| $MgSO_4.7H_2O$ | 400 | 200 | 400 | 400 | 200 | 133.3 |
| $MnSO_4.H_2O$ | 10 | 5 | 10 | 10 | 5 | 3.3 |
| $ZnSO_4.H_2O$ | 1 | 0.5 | 1 | 1 | 0.5 | 0.33 |
| $CuSO_4.H_2O$ | 0.2 | 0.1 | 0.2 | 0.2 | 0.1 | 0.066 |
| $Na_2EDTA$ | 37.3 | 37.3 | 37.3 | 37.3 | 37.3 | 37.3 |
| $FeSO_4.7H_2O$ | 27.8 | 27.8 | 27.8 | 27.8 | 27.8 | 27.8 |
| $H_3BO_3$ | 5 | 2.5 | 5 | 5 | 5 | 5 |
| KI | 1 | 0.5 | 1 | 1 | 1 | 1 |
| $NaMoO_4.2H_2O$ | 0.1 | 0.05 | 0.1 | 0.1 | 0.1 | 0.1 |
| $CoCl_2.6H_2O$ | 0.1 | 0.05 | 0.1 | 0.1 | 0.1 | 0.1 |

[1] mg/L of salt in final medium

TABLE III

Vitamins, Hormones, and Other Nutrients in *Pinus taeda* Culture Media[1]

| Compound | Shoot Elongation Medium-I | Bud Induction Medium-I | Bud Induction Medium-II | Shoot Elongation Medium-II | Root Induction Medium | Root Growth Medium |
|---|---|---|---|---|---|---|
| Myo-inosotol | 250 | 100 | 100 | 100 | 100 | 250 |
| Thiamine.HCl | 5 | 5 | 5 | 5 | 5 | 5 |
| Nicotinic Acid | 5 | 5 | 5 | 5 | 5 | 5 |
| Pyridoxine.HCl | 0.5 | 0.5 | 0.5 | 0.5 | 0.5 | 0.5 |
| L-Glutamine | 200 | 200 | 200 | 200 | 100 | — |
| L-Asparganine | 200 | — | 200 | 200 | — | — |
| Sucrose | 30,000 | 30,000 | 30,000 | 30,000 | 15,000 | 30,000 |
| Agar | 4,000 | 4,000 | 4,000 | 4,000 | 4,000 | 4,000 |
| $N^6$-benzylaminopurine | — | — | 5 | — | — | — |
| Indole-3-butyric acid | — | — | — | — | 3 | — |
| α-Naphthalene acetic acid | — | — | 0.001 | — | 0.1 | — |
| Activated charcoal[2] | — | — | — | 10,000 | — | — |

[1] mg/L of compound in medium
[2] HCl washed

After sterilization, the explants were rinsed six times in sterile water. From 1–2 mm was then cut from the base of the shoots and they were placed base down in Shoot Elongation Medium-I of Tables II and III contained in 100×25 mm sealed Petri dishes. The culture room was maintained at about 21° C. with a 16 hour ment of additional latent axillary buds. Alternatively, the cytokinin dip can be omitted and the shoots can be placed on Bud Induction Medium-II which contains small quantities of phytohormones. The dip treatment generally gives better results and is preferred with most species.

In the budding medium, clusters of buds will form at the primary needle axils. Typically from 50 to 160 buds will form on a 4-cm long shoot during the four to six weeks residence in this medium.

Upon removal from the budding medium the shoots are cut into short sections at the internodes. These sections are then placed on Shoot Elongation Medium-II in 100×25 mm sealed dishes for a time usually about six to eight weeks. It has been found helpful to include activated charcoal in this medium to absorb toxic metabolites of the growing tissue. Each bud will elongate into a juvenile-like shoot from 1-2 cm in overall length. These shoots are then cut individually from the mass and placed base down in the auxin-containing Root Induction Medium of Tables II and III. This step is conveniently carried out in 90×95 mm culture jars.

In about four weeks from 1 to 4 short roots will have formed on the shoots. These roots are normally unbranched so the new plantlets are not yet well equipped to be thrust into a hostile outside environment. While they may be planted at this time, considerably higher survival can be achieved if the plantlets are placed in a Root Growth Medium, such as that described in Tables II and III. This is contained in the same size jars as above. Normally two to four weeks in this medium will be adequate to give the plantlet a healthy root system to better insure its future vigor.

Finally, the plantlets are placed in soil or preferably in a 1:3:1 perlite:peat:vermiculite potting mixture. They may initially be held on a mist bench for several weeks and then they are allowed to harden somewhat before being outplanted as plantlings.

EXAMPLE II

The procedure of the previous example was carried out using coast redwood (*Sequoia sempervirens*) of at least 10 years age as the donor tree. This was sprayed as before with the 200 mg/L BA solutions at weekly intervals and under the same conditions of dormancy, temperature, and photoperiod as was the *Pinus taeda*. After three to four weeks, budding was evident at the needle axils and these buds soon gave way to short juvenile-appearing shoots about 3 cm long. Procedures from this point were carried out similarly to those described in Example 1 except as noted below. The extended period after the last hormone spray and before the explants were taken from the donor tree was not felt to be necessary and the shoots were removed about six weeks after the initial cytokinin spray. Compositions of the media used are given in Tables IV and V.

TABLE IV

Salt Concentrations in *Sequoia sempervirons* Culture Media[1]

| Compound | Shoot Elongation Medium-I | Bud Induction Medium-I | Bud Induction Medium-II | Shoot Elongation Medium-II | Root Induction Medium | Root Growth Medium |
|---|---|---|---|---|---|---|
| $NH_4H_2PO_4$ | — | 300 | — | 300 | — | — |
| $NH_4NO_3$ | 825 | — | 1650 | — | — | 550 |
| $KNO_3$ | 950 | 2500 | 1900 | 2500 | 187.5 | 633.3 |
| $Ca(NO_3)_2 \cdot 4H_2O$ | 220 | — | — | — | 152 | — |
| $CaCl_2 \cdot 2H_2O$ | — | 200 | 440 | 200 | — | 146.6 |
| $NaH_2PO_4 \cdot H_2O$ | — | — | — | — | 138 | — |
| $KH_2PO_4$ | 85 | — | 170 | — | — | 56.6 |
| $MgSO_4 \cdot 7H_2O$ | 400 | 400 | 400 | 400 | 200 | 133.3 |
| $MnSO_4 \cdot H_2O$ | 10 | 10 | 10 | 10 | 5 | 3.3 |
| $ZnSO_4 \cdot H_2O$ | 1 | 1 | 1 | 1 | 0.5 | 0.33 |
| $CuSO_4 \cdot H_2O$ | 0.2 | 0.2 | 0.2 | 0.2 | 0.1 | 0.066 |
| $Na_2EDTA$ | 37.3 | 37.3 | 37.3 | 37.3 | 37.3 | 37.3 |
| $FeSO_4 \cdot 7H_2O$ | 27.8 | 27.8 | 27.8 | 27.8 | 27.8 | 27.8 |
| $H_3BO_3$ | 5 | 5 | 5 | 5 | 5 | 5 |
| KI | 1 | 0.5 | 1 | 1 | 1 | 1 |
| $NaMoO_4 \cdot 2H_2O$ | 0.1 | 0.01 | 0.1 | 0.1 | 0.1 | 0.1 |
| $CoCl_2 \cdot 6H_2O$ | 0.1 | 0.01 | 0.1 | 0.1 | 0.1 | 0.1 |

[1] mg/L of salt in medium

TABLE V

Vitamins, Hormones, and Other Nutrients in *Sequoia sempervirons* Culture Media[1]

| Compound | Shoot Elongation Medium-I | Bud Induction Medium-I | Bud Induction Medium-II | Root Induction Medium | Root Growth Medium |
|---|---|---|---|---|---|
| Myo-inosotol | 250 | 1,000 | 250 | 100 | 250 |
| Thiamine.HCl | 5 | 5 | 5 | 5 | 5 |
| Nicotinic Acid | 5 | 5 | 5 | 5 | 5 |
| Pyridoxine.HCl | 0.5 | 0.5 | 0.5 | 0.5 | 0.5 |
| L-Glutamine | — | 200 | — | 100 | — |
| L-Asparganine | — | — | — | 100 | — |
| Sucrose | 30,000 | 30,000 | 30,000 | 15,000 | 30,000 |
| Agar | 4,000 | 4,000 | 4,000 | 4,000 | 4,000 |
| $N^6$benzylamiopurine | 1.1 | — | — | — | — |
| Indole-3-acetic acid | 1 | — | — | — | — |
| Indole-3-butyric acid | 1 | — | 1 | 3 | — |
| α-Naphthalene acetic acid | — | — | 1 | 0.01 | — |
| Activated charcoal[2] | — | 10,000 | — | — | — |

[1] mg/L of compound in medium
[2] HCl washed

Because of the vigor of the shoots, an initial period in Shoot Elongation Medium was not necessary and they were placed directly in the first Bud Induction Medium of Tables IV and V. This medium contains both a cytokinin and auxins and a prior BA dip treatment was not needed. After four weeks in the budding medium, each shoot had from 15 to 30 buds. These were then placed in the first Shoot Elongation Medium for an additional four weeks. The shoots grown during this time can be excised directly from the tissue mass and placed directly in a Root Induction Medium. That route was not followed in this example, however, The shoots from the previous step were excised and given a short dip in a 50 mg/L BA solution. They were then placed again in a Bud Induction Medium in order to achieve a second order multiplication of the clone. After six weeks in this medium, they were placed in the second Shoot Elongation Medium and from there went for four to six weeks into the Root Induction Medium. Finally, after a four-week period in the Root Growth Medium, they were ready for planting in the potting mix. By this second order regneration procedure, it is theoretically possible to obtain as many as 2,500 plantlings from each original axillary bud meristem on the donor tree.

EXAMPLE 3

The procedure of Example 1 was successfully carried out on *Pinus caribaea*, an important tropical and semi-tropical timber species, and *Juniperus sabina* var. *Tamariscifolia*, a popular ornamental. In the case of these species, the juvenile-like shoots from the shoot elongation medium were placed directly in the root induction medium without the intermediate bud multiplication step. The donor stock of the Caribbean pine was about two years old, while the age of the juniper was unknown, although the plant had obvious mature characteristics.

EXAMPLE 4

*Pinus sylvestris* (Scots pine) from 4-year-old stock was successfully propagated through the first shoot elongation medium. At the time of the present writing work had not proceeded beyond this stage.

EXAMPLE 5

*Pseudotsuga menziesii* (Douglas-fir) has been successfully propagated through the bud elongation stage as of this writing. This is of particular interest for this important timber species since the physiological age of the tissue donor trees was 11 years, based on 9-year-old scions grafted two years before the present work was carried out. These trees were about five to six weeks before normal bud-break time when the first treatment began. It is of note that not only did axillary buds enlarge in the shoot growth medium, but numerous adventitious buds also formed on the bases of the needles.

EXAMPLE 6

Fascicular shoots have also been formed on 3-year-old *Pinus ponderosa* after six BA spray treatments. These have not yet been placed in culture as of the time of the present writing.

EXAMPLE 7

Axillary buds have been formed on 3-year-old *Picea sitchensis* (Sitka spruce) after four to six sprayings with 200 mg/L BA solution. These have not yet been placed in culture.

EXAMPLE 8

*Thuja plicata* (western red cedar) about thee years of age responded after three sprayings of BA solution by profuse epicormic and other adventitious budding and shoot elongation. The shoots had leaves with the needle-like morphology of newly sprouted seeds rather than the compressed scales of a mature tree. These shoots have not yet been placed in culture.

EXAMPLE 9

Araucaria either *excelsa* or *heterophylla* (Norfolk Island pine, fam. Araucariaceae) is an important southern hemisphere timber tree as well as a very popular indoor ornamental. To date it has been satisfactorily reproduced only from seed. Cuttings can be rooted with difficulty, but unless these are taken from the leader (which essentially destroys the donor tree) they exhibit severe plagiotropy (horizontal growth) after rooting. No reference has been found in the literature to the successful reproduction of any species in this family by tissue culture.

A Norfolk Island pine of mature characteristics but unknown age responded by profuse budding after three BA sprayings. As of this writing, these buds have not yet been placed in culture, but this appears to be a route whereby this tree can be successfully asexually reproduced.

It should be apparent that the method of bud or shoot induction followed by multiplication in tissue culture can be carried out on many species not disclosed in the examples. Many departures from the specific procedures described will be readily apparent to those skilled in the art. The scope of the invention should be considered as being limited only by the following claims.

What is claimed is:

1. A method for asexually reproducing coniferous trees which comprises:
   a. repetitively treating living trees with a cytokinin until buds or shoots are induced at locations where vegetative buds do not normally form, the number of treatments and intervals between treatments being selected so as to produce buds giving rise to shoots having predominantly juvenile-type morphology;
   b. excising the juvenile-type buds or shoots from the trees; and
   c. placing the excised tissue on a growth medium in order to maintain the juvenile condition and elongate shoots suitable for rooting or further multiplication in tissue culture.

2. The method of claim 1 in which the treatment interval is not less than 4 days.

3. The method of claim 1 in which the treatment interval is between 4 and 14 days.

4. The method of claim 1 in which the cytokinin comprises $N^6$-benzyladenine.

5. The method of claim 1 in which the cytokinin is applied as a solution at a concentration at least as high as $10^{-4}$ molar.

6. The method of claim 5 in which a minor percentage of N-dimethylaminosuccinamic acid is present with the cytokinin.

7. The method of claims 1, 2, 3, 4, 5, or 6 in which the cytokinin is applied in a solution by dipping or spraying that portion of the tree being treated with an amount of solution sufficient to cause runoff.

8. The method of claims 1, 2, 3, 4, 5, or 6 in which the cytokinin is applied in a solution by direct infusion into the vascular system.

9. The method of claim 1 in which the trees are members of the families Pinaceae, Cupressaceae, or Taxodiaceae.

10. The method of claim 9 in which the trees are from the genera Pinus or Thuja.

11. The method of claim 10 in which the cytokinin treatments are continued until the newly formed buds elongate into primary shoots before they are excised from the trees.

12. The method of claim 11 in which the excised shoots are placed in a growth medium for further elongation, then the elongated shoots are placed in a bud induction medium to bring about formation of axillary buds.

13. The method of claim 12 in which the elongated shoots are given a one-time cytokinin treatment between the growth and budding media.

14. The method of claims 12 or 13 in which the budded shoots are further placed on a shoot elongation medium to bring about development of additional juvenile-like shoots.

15. The method of 14 in which the additional juvenile-like shoots are excised and placed in an auxin containing medium for rooting.

16. The method of claim 9 in which the trees are from the genera Picea, Tsuga, Pseudotsuga, Thuja, Juniperus, or Sequoia.

17. The method of claim 16 in which the cytokinin treatments are continued only until axillary or adventitious buds develop on the living tree and the buds are excised and put into growth medium to induce bud growth and shoot elongation.

18. The method of claim 17 in which the shoots are excised and placed in an auxin containing medium for rooting.

19. The method of claim 1 in which the trees are members of the family Araucariaceae.

20. The method of claim 19 in which the trees are from the genus Araucaria.

* * * * *